US010981861B1

(12) United States Patent
Zhu et al.

(10) Patent No.: US 10,981,861 B1
(45) Date of Patent: *Apr. 20, 2021

(54) BROMINATION METHOD FOR M-DIAMIDE COMPOUNDS

(71) Applicant: Chang Sha Jia Qiao Biotech CO., LTD., Hunan Province (CN)

(72) Inventors: Jintao Zhu, Hunan Province (CN); Liang Lv, Shanghai (CN); Chaoqun Huang, Hunan Province (CN); Liangming Luo, Hunan Province (CN); Rong Zhang, Hunan Province (CN)

(73) Assignee: Chang Sha Jia Qiao Biotech CO., LTD., Hunan Province (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/842,069

(22) Filed: Apr. 7, 2020

(30) Foreign Application Priority Data

Oct. 25, 2019 (CN) .......................... 201911023384.8

(51) Int. Cl.
*C07C 231/12* (2006.01)
*C07C 237/42* (2006.01)

(52) U.S. Cl.
CPC .......... *C07C 231/12* (2013.01); *C07C 237/42* (2013.01)

(58) Field of Classification Search
None
See application file for complete search history.

(56) References Cited

U.S. PATENT DOCUMENTS

2015/0065721 A1* 3/2015 Okura .................. C07C 231/12
546/300

FOREIGN PATENT DOCUMENTS

| EP | 2835366 | 2/2015 |
|----|---------|--------|
| JP | S5262201 | 5/1977 |
| JP | S6075443 | 4/1985 |
| JP | H0827054 | 1/1996 |
| JP | 2000516941 | 12/2000 |
| JP | 2006111595 | 4/2006 |
| JP | 2009013158 | 1/2009 |
| JP | 2011529939 | 12/2011 |
| WO | 2004/103947 | 12/2004 |
| WO | 2013150988 | 10/2013 |

OTHER PUBLICATIONS

Lau ("1,3,5-Trimethoxybenzene (TMB) as a new quencher for preserving redox-labile disinfection byproducts and for quantifying free chlorine and free bromine" Environmental Science Water Research and Technology, 2018, vol. 4, p. 926-941). (Year: 2018).*
Clark ("Halogens as Oxidizing Agents", downloaded from: https://chem.libretexts.org/@go/page/3697on Oct. 8, 2020) (Year: 2020).*
Extended European Search Report issued in 20164183.4, dated Aug. 27, 2020.
Roche D et al. "Mild and regioselective oxidative bromination of anilines using potassium bromide and sodium perborate", Tetrahedron Letters, Elsevier Ltd, Amsterdam, NL, vol. 41, No. 13, Mar. 1, 2000 (Mar. 1, 2000), pp. 2083-2085, XP004192680, ISSN: 0040-4039, DOI: 10.1016/S0040-4039(00)00119-2.
Ajda Podgorsek et al. "Oxidative Halogenation with "Green" Oxidants: Oxygen and Hydrogen Peroxide", Angewandte Chemie, International Edition, vol. 48, No. 45, Oct. 26, 2009 (Oct. 26, 2009), pp. 8424-8450, XP55700846, DE ISSN: 1433-7851, DOI: 10.1002/anie.200901223.

* cited by examiner

*Primary Examiner* — Amy C Bonaparte
(74) *Attorney, Agent, or Firm* — Barnes & Thornburg LLP; Jeffrey R. Stone

(57) ABSTRACT

The present disclosure provides a bromination method for m-diamide compounds comprising reacting a compound represented by formula I with a brominating reagent in the presence of an oxidant to obtain a brominated product represented by formula II. The method adopts a special design of brominating reagents and reaction conditions to introduce a bromine atom at a specific site of the m-diamide compound, with 87.9 to 99.5% yield of a brominated product obtained by the reaction and higher than 91.8% purity. Therefore, the bromination method has a simple route, mild reaction conditions, high efficiency, and does not require complicated and cumbersome post-treatment processes; furthermore, raw materials used for the bromination reaction are readily available, costs of the brominating reagent are low, and the brominated product finally obtained has high yield and high purity, thus the method is a novel one with a broad application prospect.

19 Claims, No Drawings

BROMINATION METHOD FOR M-DIAMIDE COMPOUNDS

CROSS-REFERENCE TO RELATED APPLICATIONS

The application claims the benefit of the earlier filing date of Chinese Patent Application No. 201911023384.8, filed on Oct. 25, 2019 to the China National Intellectual Property Administration, the entire contents of which are incorporated by reference herein.

TECHNICAL FIELD

The present disclosure belongs to the technical field of organic synthesis, and in particular relates to a bromination method for m-diamide compounds.

BACKGROUND

Diamide insecticides belong to a new type of high-efficiency insecticides developed from the end of 1990s to the early 21st century. An advent of this type of insecticides marks an entry of chemical pesticides into a microtoxicity era. Its representative species include flubendiamide and chlorantraniliprole. With an increasing pressure of environmental protection and rising insecticidal resistance, existing diamide insecticides have been encountering many problems and pressures. Due to high toxicity to aquatic organisms, the United States cancelled the registration of flubendiamide on more than 200 crops in 2016, and China cancelled its registration on rice and banned the use of flubendiamide on rice crops from Oct. 1, 2018. Therefore, it is an urgent demand in the field of chemical pesticides to find a new type of insecticide with high efficiency, low toxicity, environmental friendliness and a new mechanism of action. M-diamide compounds represented by Broflanilide are increasingly becoming research hotspots of pesticide companies at home and abroad due to their characteristics such as unique action mechanism, novel action target and environmental friendliness.

M-diamide compounds represented by Broflanilide, which has a meta-formamide benzamide structure and an active metabolite of gamma-aminobutyric acid (GABA) gated chloride channel allosteric regulator, have higher selectivity to GABA and characteristics of broad spectrum and high efficiency. Guided by novel action mechanism of m-diamide insecticides, more pesticide chemical companies are committed to developing more types of new m-diamide insecticides that have fast-acting and high insecticidal activity at low doses.

CN104245665A discloses a method for producing an alkylated aromatic amide derivative, and specifically discloses a synthetic route of Broflanilide, that is, firstly obtaining 2-fluoro-3-(N-methylbenzamido)-N-[2-(trifluoromethyl)phenyl]benzamide through the reaction of 2-(trifluoromethyl)aniline, triethylamine, and 2-fluoro-3-(N-methylbenzamido)benzoylchloride, and then reacting 2-fluoro-3-(N-methylbenzamido)-N-[2-(trifluoromethyl)phenyl]benzamide with heptafluoroisopropyl iodide to give 2-fluoro-3-(N-methylbenzamido)-N-[2-(trifluoromethyl)-4-(heptafluoroisopropyl)phenyl]benzamide, which is finally brominated with bromobutadienamine (NBS) to give Broflanilide. However, in this synthetic route, the bromine source NBS used in the last step of bromination reaction is expensive, and the product yield is only 56%, which is not suitable for industrial applications.

In the method for preparing Broflanilide disclosed in EP2319830A1, an intermediate 2-bromo-4-heptafluoroisopropyl-6-trifluoromethylaniline is obtained by a bromination reaction between 4-(perfluoropropane-2-yl)-2-trifluoromethylaniline and NBS, with a yield of only 80%. Not only reaction conditions for subsequent preparation of m-diamide involve low temperature environment, harsh preparing process and complicated post-treatment, but the yield of the final product is only 70%, which make it difficult to be used for large-scale industrial production.

CN109497062A discloses a m-diamide compound, a method for preparing the same, and an application thereof. The m-diamide compound has not only a high insecticidal activity at a low dose, but good fast-acting properties. However, in preparation of the m-diamide compound, an intermediate 2-bromo-4-heptafluoroisopropyl-6-trifluoromethylaniline is used to prepare the in-diamide compound with a yield of only 13-28%. Moreover, the product ought to be purified by column chromatography. Costs of raw materials, equipments and time of the preparation method are high, which make the method not suitable for industrial scale-up.

In summary, for the existing preparation processes of m-diamide compounds, bromination reagents required for the bromination reaction are expensive, yields of brominated products are low, synthetic routes for preparing the final target product m-diamide compounds are long, reaction conditions are difficult to control, and post-treatment procedures are complicated. Thus the industrial production of m-diamide compounds has problems of high costs of raw materials, equipments and time.

Therefore, it is a research focus in this field to develop a bromination method for m-diamide compounds with high yield, low cost, simple synthetic route and mild reaction conditions to realize a large-scale industrial production of in-diamide insecticides.

SUMMARY

The present disclosure provides a bromination method for m-diamide compounds. By designing brominating reagents and reaction conditions, a bromine atom is introduced at a specific site of the m-diamide compound to obtain a brominated product with a high yield. The bromination method has advantages of a simple synthetic route, mild conditions, low cost, high yield and high purity of the brominated product, which make it a broad industrial application prospect.

To achieve this object, the present disclosure adopts the following technical solutions:

The present disclosure provides a bromination method for m-diamide compounds. The bromination method comprises: reacting a compound represented by formula I with a brominating reagent in the presence of an oxidant to obtain a brominated product represented by formula II, the reaction scheme is as follows:

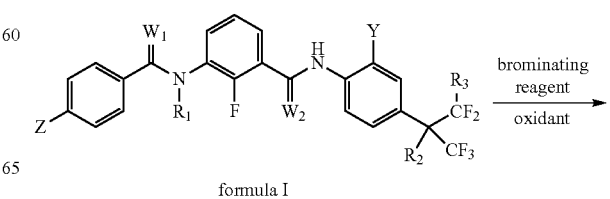

formula I

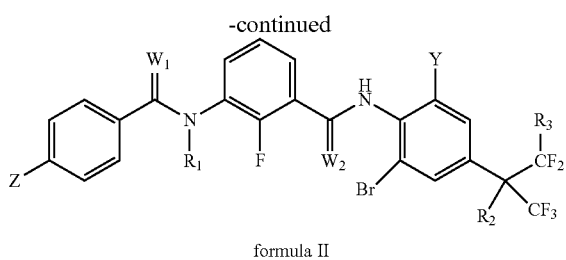

formula II wherein, Z is selected from any one of the group consisting of hydrogen, halogen, cyano, nitro, C1-C6 (e.g., C1, C2, C3, C4, C5 or C6) linear or branched alkyl, halogenated C1-C6 (e.g., C1, C2, C3, C4, C5 or C6) linear or branched alkyl, C1-C6 (e.g., C1, C2, C3, C4, C5 or C6) linear or branched alkoxyl, halogenated C1-C6 (e.g., C1, C2, C3, C4, C5 or C6) linear or branched alkoxyl, C1-C6 (e.g., C1, C2, C3, C4, C5 or C6) alkylsulfonyl, halogenated C1-C6 (e.g., C1, C2, C3, C4, C5 or C6) alkylsulfonyl, C1-C6 (e.g., C1, C2, C3, C4, C5 or C6)alkylsulfinyl, and halogenated C1-C6 (e.g., C1, C2, C3, C4, C5 or C6) alkylsulfinyl.

$W_1$ and $W_2$ are each independently O or S.

$R_1$ is selected from any one of the group consisting of C1-C6 (e.g., C1, C2, C3, C4, C5 or C6) linear or branched alkyl, and

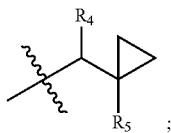

$R_4$ is selected from the group consisting of hydrogen, halogen, C1-C6 linear or branched alkyl, halogenated C1-C6 (e.g., C1, C2, C3, C4, C5 or C6) linear or branched alkyl, C3-C8 (e.g., C3, C4, C5, C6, C7 or C8) cycloalkyl, and halogenated C3-C8 (e.g., C3, C4, C5, C6, C7 or C8) cycloalkyl; $R_5$ is hydrogen or halogen; and the wavy line represents the connecting site of a group.

Y is selected from any one of the group consisting of halogen, C1-C6 (e.g., C1, C2, C3, C4, C5 or C6) linear or branched alkyl, halogenated C1-C6 (e.g., C1, C2, C3, C4, C5 or C6) linear or branched alkyl, C1-C6 (e.g., C1, C2, C3, C4, C5 or C6) linear or branched alkoxyl, and halogenated C1-C6 (e.g., C1, C2, C3, C4, C5 or C6) linear or branched alkoxyl.

$R_2$ is hydrogen, halogen or methoxyl.

$R_3$ is fluoro or trifluoromethyl.

In the present disclosure, the halogen is fluorine, chlorine, bromine or iodine. The C1-C6 (e.g., C1, C2, C3, C4, C5, or C6) linear or branched alkyl exemplarily includes but is not limited to methyl, ethyl, n-propyl, isopropyl, n-butyl, isobutyl, sec-butyl, tert-butyl, n-pentyl, iso-pentyl, and n-hexyl. The halogenated C1-C6 linear or branched alkyl means that at least one hydrogen in the alkyl group is replaced by a halogen atom, and exemplarily includes but is not limited to trifluoromethyl, difluoromethyl, 1,1,1-trifluoroethyl, pentafluoroethyl, heptafluoro n-propyl, and heptafluoroisopropyl. The C1-C6 (e.g., C1, C2, C3, C4, C5, or C6) linear or branched alkoxyl exemplarily includes, but is not limited to, methoxyl, ethoxyl, n-propoxyl, isopropoxyl, and tert-butoxyl. The halogenated C1-C6 (e.g., C1, C2, C3, C4, C5, or C6) linear or branched alkoxyl means that at least one hydrogen in the alkoxyl group is replaced by a halogen atom. The C3-C8 (e.g., C3, C4, C5, C6, C7 or C8) cycloalkyl exemplarily includes but is not limited to cyclopropyl, cyclobutyl, cyclopentyl, cyclohexyl, cycloheptyl, and cyclooctyl. The halogenated C3-C8 (e.g., C3, C4, C5, C6, C7, or C8) cycloalkyl means that at least one hydrogen in the cycloalkyl group is replaced with a halogen atom, and exemplarily includes but is not limited to 1-chlorocyclopropyl, 1-fluorocyclopropyl, perfluorocyclopropyl, 1-chlorocyclobutyl, and 1-chlorocyclopentyl.

Preferably, the brominating reagent is metal bromide, ammonium bromide, bromine, or hydrobromic acid.

Preferably, the metal is an alkali metal or an alkaline earth metal.

Preferably, the brominating agent is sodium bromide, potassium bromide, bromine or hydrobromic acid.

Preferably, the molar ratio of the brominating reagent to the compound represented by formula I is from 0.55:1 to 2.0:1, for example 0.6:1, 0.7:1, 0.8:1, 0.9:1, 1:1, 1.1:1, 1.2:1, 1.3:1, 1.4:1, 1.5:1, 1.6:1, 1.7:1, 1.8:1, or 1.9: 1.

In the present disclosure, the molar amount of the brominating reagent is calculated based on the effective component containing bromine. For an instance, when the brominating reagent is hydrobromic acid, its molar amount is calculated based on the molar amount of HBr.

Preferably, the oxidant is selected from any one or a combination of at least two of the group consisting of metal perchlorate, metal chlorate, metal hypochlorite, and chlorine.

Preferably, the metal is an alkali metal or an alkaline earth metal.

Preferably, the oxidant is selected from the group consisting of metal chlorate, metal hypochlorite, and chlorine.

Preferably, the oxidant is selected from the group consisting of sodium chlorate, potassium chlorate, sodium hypochlorite, potassium hypochlorite, and chlorine.

Preferably, the molar ratio of the oxidant to the compound represented by formula I is from 0.4:1 to 2.0:1, for example 0.5:1, 0.6:1, 0.7:1, 0.8:1, 0.9:1, 1:1, 1.1:1, 1.2:1, 1.3:1, 1.4:1, 1.5:1, 1.6:1, 1.7:1, 1.8:1, or 1.9:1.

Preferably, the reaction is performed in the presence of an alkaline compound.

Preferably, the alkaline compound is selected from any one or a combination of at least two of the group consisting of metal hydroxide, metal carbonate, metal bicarbonate, and ammonia.

Preferably, the metal is an alkali metal or an alkaline earth metal.

Preferably, the alkaline compound is metal hydroxide, and further preferably sodium hydroxide or potassium hydroxide.

Preferably, the molar ratio of the alkaline compound to the compound represented by formula I is from 0.1:1 to 2.0:1, for example 0.2:1, 0.3:1, 0.4:1, 0.5:1, 0.6:1, 0.7:1, 0.8:1, 0.9:1, 1:1, 1.1:1, 1.2:1, 1.3:1, 1.4:1, 1.5:1, 1.6:1, 1.7:1, 1.8:1, or 1.9:1.

Preferably, the reaction is performed in the presence of a solvent.

Preferably, the solvent is selected from any one or a combination of at least two of the group consisting of haloalkane solvents, aromatic hydrocarbon solvents, alcoholic solvents, chain or cyclic ether solvents, and nitrile solvents.

Preferably, the haloalkane solvent is selected from any one or a combination of at least two of the group consisting of dichloromethane, 1,2-dichloroethane, chloroform, and carbon tetrachloride.

Preferably, the aromatic hydrocarbon solvent is selected from any one or a combination of at least two of the group consisting of benzene, toluene, xylene, chlorobenzene, and dichlorobenzene, and further preferably toluene.

Preferably, the alcoholic solvent is selected from any one or a combination of at least two of the group consisting of methanol, ethanol, n-propanol, isopropanol, n-butanol, isobutanol, and tert-butanol, and further preferably tert-butanol.

Preferably, the chain or cyclic ether solvent is selected from any one or a combination of at least two of the group consisting of diethyl ether, tetrahydrofuran, dioxane, and 1,2-dimethoxyethane, and further preferably diethyl ether.

Preferably, the nitrile solvent is selected from any one or a combination of at least two of the group consisting of acetonitrile, propionitrile, and butyronitrile, and further preferably acetonitrile.

Preferably, based on 1 mol of the amount of the compound represented by formula I, the amount of the solvent is from 500 g to 3500 g, for example, 600 g, 800 g, 1000 g, 1200 g, 1500 g, 1800 g, 2000 g, 2300 g, 2500 g, 2800 g, 3000 g, 3200 g, 3500 g, 3800 g, 4000 g, 4300 g, 4500 g, 4700 g, or 4900 g.

As a preferred technical solution of the present disclosure, Z is selected from any one of the group consisting of hydrogen, fluorine, chlorine, bromine, iodine, cyano, nitro, fluorinated C1-C4 (e.g., C1, C2, C3, or C4) linear or branched alkyl, fluorinated C1-C4 (e.g., C1, C2, C3 or C4) linear or branched alkoxyl, C1-C4 (e.g., C1, C2, C3 or C4) alkylsulfonyl, and fluorinated C1-C4 (e.g., C1, C2, C3 or C4) alkylsulfonyl.

As the preferred technical solution of the present disclosure, Z is selected from any one of the group consisting of hydrogen, fluorine, chlorine, bromine, iodine, cyano, nitro, trifluoromethyl, pentafluoroethyl, heptafluoroisopropyl, difluoromethoxyl, trifluoromethoxyl, methylsulfinyl, trifluoromethylsulfinyl, methanesulfonyl, and trifluoromethanesulfonyl.

Preferably, Z is selected from any one of the group consisting of hydrogen, fluorine, chlorine, bromine, cyano, trifluoromethyl, trifluoromethoxyl, and methanesulfonyl.

Preferably, both of $W_1$ and $W_2$ are O.

Preferably, $R_1$ is selected from any one of C1-C4 (e.g., C1, C2, C3 or C4) linear or branched alkyl, and

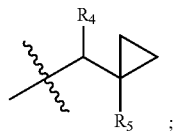

$R_4$ is selected from the group consisting of hydrogen, fluorine, methyl, ethyl, n-propyl, isopropyl, n-butyl, or isobutyl, tert-butyl, n-pentyl, 2-pentyl, neopentyl, isopentyl, 4-methyl-2-pentyl, n-hexyl, monofluoromethyl, difluoromethyl, trifluoromethyl, monochloromethyl, dichloromethyl, trichloromethyl, pentafluoroethyl, heptafluoroisopropyl, cyclopropyl, cyclobutyl, cyclopentyl, perfluorocyclopropyl, perfluorocyclobutyl, and perfluorocyclopentyl; $R_5$ is hydrogen, fluorine or chlorine; the wavy line represents the connecting site of a group.

Preferably, $R_1$ is methyl, cyclopropylmethyl or 1-cyclopropylethyl.

Preferably, Y is selected from any one of the group consisting of halogen, C1-C4 (e.g., C1, C2, C3, or C4) linear or branched alkyl, fluorinated C1-C4 (e.g., C1, C2, C3, or C4) linear or branched alkyl, C1-C4 (e.g., C1, C2, C3, or C4) linear or branched alkoxyl, and fluorinated C1-C4 (e.g., C1, C2, C3, or C4) linear or branched alkoxyl.

As a preferred technical solution of the present disclosure, Y is selected from any one of the group consisting of fluorine, chlorine, bromine, iodine, methyl, ethyl, trifluoromethyl, pentafluoroethyl, heptafluoroisopropyl, methoxyl, ethoxyl, difluoromethoxyl, and trifluoromethoxyl.

Preferably, Y is trifluoromethyl.

Preferably, $R_2$ is fluorine.

Preferably, $R_3$ is fluorine.

Preferably, the reaction temperature is from 0 to 150° C., for example, 1° C., 5° C., 10° C., 15° C., 20° C., 25° C., 30° C., 35° C., 40° C., 45° C., 50° C., 55° C., 60° C., 65° C., 70° C., 75° C., 80° C., 85° C., 90° C., 95° C., 100° C., 110° C., 120° C., 130° C., 140° C., or 145° C., and further preferably from 35 to 90° C.

Preferably, the reaction time is from 0.5 to 8 h, for example, 0.6 h, 0.8 h, 1 h, 1.3 h, 1.5 h, 1.8 h, 2 h, 2.5 h, 3 h, 4 h, 5 h, 6 h, 7 h, or 7.5 h, and further preferably from 1 to 2 h.

Preferably, the oxidant is added by pipeline or dropwise addition.

In the present disclosure, the oxidant is selected from any one or a combination of at least two of the group consisting of metal perchlorate, metal chlorate, metal hypochlorite, and chlorine. The metal salt of the oxidant can be mixed with water to form an oxidant aqueous solution followed by dropwise addition to the reaction; when the oxidant contains chlorine gas, the chlorine gas is charged to the reaction by pipeline.

Preferably, the bromination method further comprises post-treatment steps.

Preferably, the post-treatment steps include organic phase separation, washing, solvent removal and drying.

Preferably, the solution for washing is sodium sulfite solution.

Preferably, the concentration of the sodium sulfite solution is from 5 to 20%, for example, 6%, 8%, 10%, 12%, 14%, 16%, 18%, or 19%, and further preferably 10%.

Preferably, the bromination method is specifically as follows: a compound represented by formula I is mixed with a solvent, a brominating agent and an alkaline compound are added, an oxidant is dropwise added or charged by pipeline at 0-150° C., and then reacted at 0-150° C. for 0.5-8 hours; after the reaction is completed, the solution is separated and washed with sodium sulfite solution, then the solvent is removed and the resultant is dried to obtain the brominated product represented by formula II.

Compared with the related technics, the present disclosure has the following beneficial effects:

In the bromination method for m-diamide compounds provided by the present disclosure, a special design of brominating reagents and reaction conditions is used to introduce a bromine atom at a specific site of the m-diamide compound. The yield of the brominated product obtained by the reaction can reach 87.9 to 99.5% and the purity 91.8 to 98.3%. Therefore, the bromination method according to the present disclosure has a simple synthetic route, mild reaction conditions and high efficiency, and does not require complicated and cumbersome post-treatment processes. Moreover, raw materials used for the bromination reaction are readily available, costs of the brominating reagents are low, and the final brominated product can be prepared in high yield and purity, which make this new bromination method of the present disclosure a broad industrial application prospect.

DETAILED DESCRIPTION

The technical solutions of the present disclosure will be further described below by way of specific embodiments. It will be apparent to those skilled in the art that the embodiments are merely illustrations of the present disclosure and should not be construed as specific limitations to the present disclosure.

The experimental materials used in the following examples of the present disclosure include compounds represented by formula I, brominating reagents, oxidants, alkaline compounds and solvents. The compound represented by formula I can be commercially available, or can be prepared according to the related technics, for example, prepared according to CN104245665A. The brominating reagents, oxidants, alkaline compounds and solvents can all be commercially available.

Exemplarily, the compound represented by formula I used in Example 3 is 2-fluoro-3-(N-methylbenzamido)-N-[2-(trifluoromethyl)-4-(heptafluoroisopropyl)phenyl)benzamide, i.e., in formula I, Z is hydrogen, $W_1$ and $W_2$ are O, $R_1$ is methyl, Y is trifluoromethyl, $R_2$ and $R_3$ are fluoro.

Its preparation method is as follows:

0.8 g (20 mmol) of powdered sodium hydroxide and 0.93 g (3.3 mmol) of iron (II) sulfate heptahydrate were stirred in an ice bath until the mixture color became black; as soon as the color became black, 5 g of N, N-dimethylformamide, g (2.4 mmol) of 2-fluoro-3-(N-methylbenzamido)-N-[2-(trifluoromethyl)phenyl]benzamide and 1 g (3.4 mmol) of heptafluoroisopropyl iodide in 5 g of N, N-dimethylformamide were added. The resulting mixture was stirred at room temperature for 3 hours, filtered through celite and washed with 50 mL of ethyl acetate. The filtrate was extracted with 40 g of water; the organic phase was dried with magnesium sulfate, filtered and evaporated. The residue was purified by silica gel column chromatography to obtain 0.89 g of a white solid in yield 63%.

The compounds of formula I used in Examples 1-10 of the present disclosure can all be prepared by the above method. The corresponding raw materials are all commercially available. For brevity, they will not be described in details in the present disclosure.

In the following examples of the present disclosure, the purity of the brominated product was measured through external standard method by using high-performance organic phase chromatography (HPLC, LC-20AT, Shimadzu Corporation, Japan), and the yield is in mass.

Example 1

A bromination method for m-diamide compounds is provided in this example, the scheme is as follows:

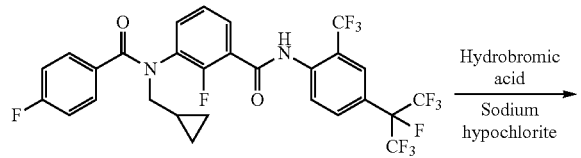

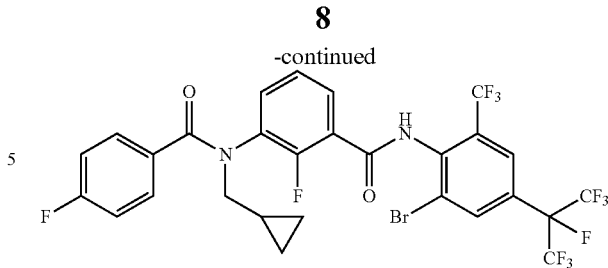

Specifically, it includes the following steps:

To a 1000 mL three-necked flask, 64.2 g (0.1 mol) of 3-(4-fluoro-N-cyclopropylmethylbenzamido)-2-fluoro-N-[4-(perfluoropropane-2-yl)-2-(trifluoromethyl)phenyl]benzamide, 200 g of carbon tetrachloride, 24.3 g (0.12 mol) of 40% hydrobromic acid, 7.1 g (0.17 mol) of sodium hydroxide, and 30 g of water were added. 149.1 g of 10% sodium hypochlorite solution was added dropwise at 60° C. and the resultant mixture was stirred at 60° C. for 1.5 h. After the reaction was completed, the organic phase was separated, washed with 100 g of 10% sodium sulfite solution, evaporated and dried to obtain 72.7 g of solid brominated product in purity 98.0% and yield 98.8%.

Characterization data: LC/MS [M+1]: m/z=722;
$^1$H-NMR (DMSO-$d_6$, 400 MHz): δ 10.56 (s, 1H), 8.41 (s, 1H), 7.95 (s, 1H), 7.70-7.56 (m, 2H), 7.38-7.32 (m, 3H), 7.09 (br s, 2H), 3.69 (br s, 2H), 1.03-1.01 (m, 1H), 0.41-0.39 (m, 2H), 0.08-0.06 (m, 2H).

Example 2

A bromination method for m-diamide compounds is provided in this example, the scheme is as follows:

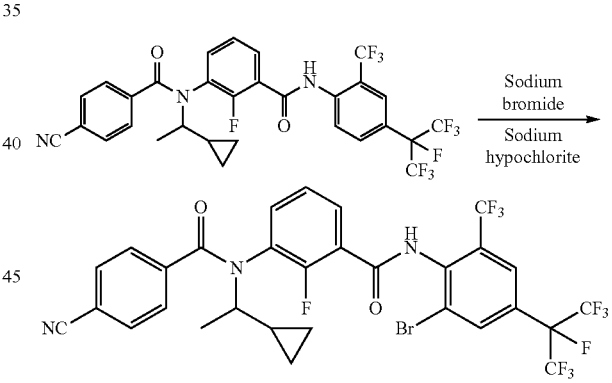

Specifically, it includes the following steps:

To a 1000 mL three-necked flask, 66.3 g (0.1 mol) of 314-cyano-N-(1-cyclopropylethyl)benzamido]-2-fluoro-N-[4-(perfluoropropane-2-yl)-2-(trifluoromethyl)phenyl]benzamide, 130 g of diethyl ether, 11.3 g (0.11 mol) of sodium bromide, and 30 g of water were added. 111.7 g of 10% sodium hypochlorite solution was added dropwise at 35° C. and the resultant mixture was stirred at 35° C. for 2 h. After the reaction was completed, the organic phase was separated, washed with 100 g of 10% sodium sulfite solution, evaporated and dried to obtain 71.9 g of solid brominated product in purity 97.1% and yield 94.1%.

Characterization data: LC/MS [M+1]: m/z=743;
$^1$H-NMR (DMSO-$d_6$, 400 MHz): δ 10.51 (d, J=27.1 Hz, 1H), 8.54-8.35 (m, 1H), 7.95 (s, 1H), 7.86-7.51 (m, 4H), 7.51-7.20 (m, 3H), 4.03 (q, J=7.1 Hz, 1H), 1.30-1.19 (m, 3H), 0.93-0.23 (m, 5H).

Example 3

A bromination method for m-diamide compounds is provided in this example, the scheme is as follows:

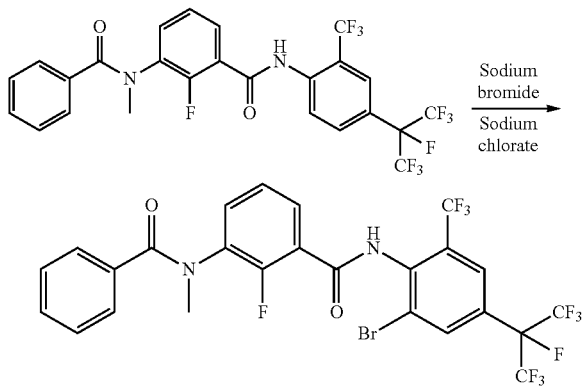

Specifically, it includes the following steps:
To a 1000 mL three-necked flask, 58.4 g (0.1 mol) of 2-fluoro-3-(N-methylbenzamido)-N-[2-(trifluoromethyl)-4-(heptafluoroisopropyl) phenyl]benzamide, 60 g of dichloromethane, 15.5 g (0.15 mol) of sodium bromide, 4.2 g (0.1 mol) of sodium hydroxide, and 40 g of water were added. 21.3 g of 20% sodium chlorate solution was added dropwise at 40° C. and the resultant mixture was stirred at 40° C. for 2 h. After the reaction was completed, the organic phase was separated, washed with 100 g of 10% sodium sulfite solution, evaporated and dried to obtain 67.1 g of solid brominated product in purity 98.3% and yield 99.5%.

Characterization data: LC/MS [M+1]: m/z=664;
$^1$H-NMR (DMSO-$d_6$, 400 MHz): δ 10.51 (s, 1H), 8.36 (s, 1H), 7.94 (s, 1H), 7.61-7.55 (m, 2H), 7.34-7.22 (m, 6H), 3.17 (s, 3H).

Example 4

A bromination method for m-diamide compounds is provided in this example, the scheme is as follows:

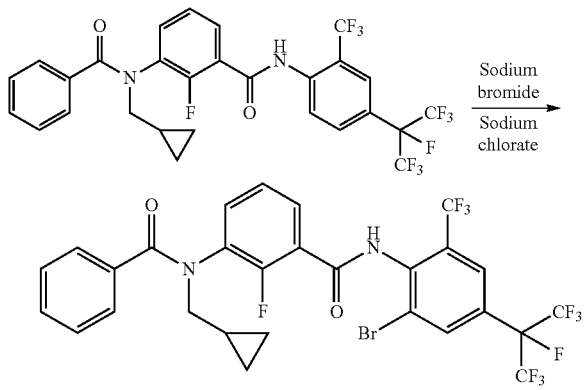

Specifically, it includes the following steps:
To a 1000 mL three-necked flask, 62.5 g (0.1 mol) of N-[2-trifluoromethyl-4-(1,1,1,2,3,3,3-heptafluoroprop-2-yl)-phenyl]-3-[N-(cyclopropylmethyl)-benzamido]-2-fluorobenzamide, 250 g of toluene, 15.5 g (0.15 mol) of sodium bromide, 4.2 g (0.1 mol) of sodium hydroxide, and 40 g of water were added. 121.5 g of 10% sodium hypochlorite solution was added dropwise at 90° C. and the resultant mixture was stirred at 90° C. for 1 h. After the reaction was completed, the organic phase was separated, washed with 100 g of 10% sodium sulfite solution, evaporated and dried to obtain 69.4 g of solid brominated product in purity 92.1% and yield 90.9%.

Characterization data: LC/MS [M+1]: m/z=704;
$^1$H-NMR (CDCl$_3$-d, 400 MHz): δ 8.15 (d, J=2.1 Hz, 1H), 8.03 (br s, 2H), 7.92 (d, J=2.1 Hz, 1H), 7.55 (br s, 1H), 7.35-7.21 (m, 5H), 3.84 (d, J=93.6 Hz, 2H), 1.14 (br s, 1H), 0.59-0.40 (m, 2H), 0.20 (d, J=42.2 Hz, 2H).

Example 5

A bromination method for m-diamide compounds is provided in this example, the scheme is as follows:

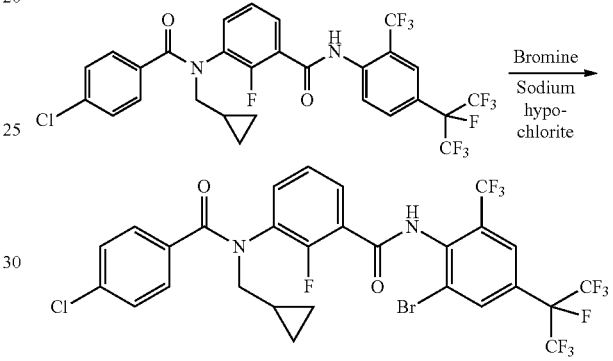

Specifically, it includes the following steps:
To a 1000 mL three-necked flask, 65.9 g (0.1 mol) of N-[2-trifluoromethyl-4-(1,1,1,2,3,3,3-heptafluoroprop-2-yl)-phenyl]-3-[N-(cyclopropylmethyl)-chlorobenzamido]-2-fluorobenzamide, 350 g of acetonitrile, 8.8 g (0.055 mol) of bromine, 4.2 g (0.1 mol) of sodium hydroxide, and 40 g of water were added. 110.8 g of 10% sodium hypochlorite solution was added dropwise at 35° C. and the resultant mixture was stirred at 35° C. for 1.5 h. After the reaction was completed, the organic phase was separated, washed with 100 g of 10% sodium sulfite solution, evaporated and dried to obtain 69.8 g of solid brominated product in purity 93.0% and yield 87.9%.

Characterization data: LC/MS [M+1]: m/z=739;
$^1$H-NMR (DMSO-$d_6$, 400 MHz): δ 8.18-7.84 (m, 4H), 7.53 (t, J=7.7 Hz, 1H), 7.37-7.07 (m, 4H), 3.81 (d, J=85.0 Hz, 2H), 1.11 (br s, 1H), 0.49 (br s, 2H), 0.17 (d, J=32.1 Hz, 2H).

Example 6

A bromination method for m-diamide compounds is provided in this example, the scheme is as follows:

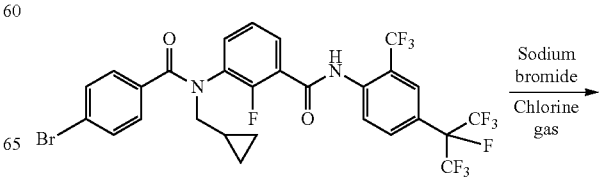

-continued

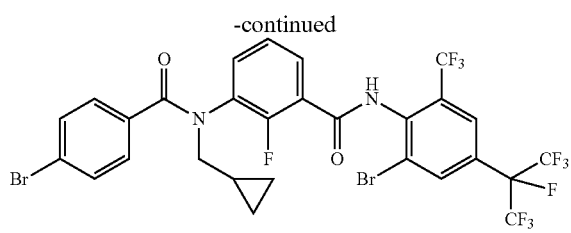

Specifically, it includes the following steps:

To a 1000 mL three-necked flask, 70.3 g (0.1 mol) of N-[2-trifluoromethyl-4-(1,1,1,2,3,3,3-heptafluoroprop-2-yl)-phenyl]-3-[N-(cyclopropylmethyl)-bromobenzamido]-2-fluorobenzamide, 400 g of 1,2-dichloroethane, 15.5 g (0.15 mol) of sodium bromide, 8.4 g (0.2 mol) of sodium hydroxide, and 40 g of water were added. 7.8 g (0.11 mol) of chlorine gas was charged at 60° C. and the resultant mixture was stirred at 60° C. for 1 h. After the reaction was completed, the organic phase was separated, washed with 100 g of 10% sodium sulfite solution, evaporated and dried to obtain 78.0 g of solid brominated product in purity 92.8% and yield 92.6%.

Characterization data: LC/MS [M+1]: m/z=783;
$^1$H-NMR (CDCl$_3$-d, 400 MHz): δ 8.13 (d, J=2.0 Hz, 1H), 8.05 (t, J=7.6 Hz, 1H), 7.90 (s, 1H), 7.54 (t, J=7.8 Hz, 1H), 7.32 (d, J=9.7 Hz, 2H), 7.21 (t, J=6.7 Hz, 3H), 3.81 (d, J=87.9 Hz, 2H), 1.10 (br s, 1H), 0.50 (br s, 2H), 0.18 (d, J=35.8 Hz, 2H).

Example 7

A bromination method for m-diamide compounds is provided in this example, the scheme is as follows:

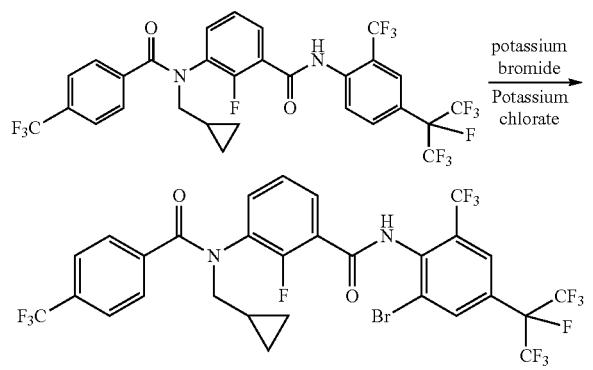

Specifically, it includes the following steps:

To a 1000 mL three-necked flask, 69.2 g (0.1 mol) of N-[2-trifluoromethyl-4-(1,1,1,2,3,3,3-heptafluoroprop-2-yl)-phenyl]-3-[N-(cyclopropylmethyl)-4-trifluoromethyl-benzamido]-2-fluorobenzamide, 450 g of chloroform, 17.9 g (0.15 mol) of potassium bromide, 3.3 g (0.05 mol) of potassium hydroxide, and 40 g of water were added. 73.5 g of 20% potassium chlorate solution was added dropwise at 60° C. and the resultant mixture was stirred at 60° C. for 1 h. After the reaction was completed, the organic phase was separated, washed with 100 g of 10% sodium sulfite solution, evaporated and then dried to obtain 78.8 g of solid brominated product in purity 91.8% and yield 93.8%.

Characterization data: LC/MS [M+1]: m/z=772;
$^1$H-NMR (CDCl$_3$-d, 400 MHz): δ 8.21-7.79 (m, 4H), 7.66-7.28 (m, 5H), 3.85 (d, J=104.7 Hz, 2H), 1.12 (br s, 1H), 0.51 (br s, 2H), 0.20 (d, J=42.7 Hz, 1H).

Example 8

A bromination method for m-diamide compounds is provided in this example, the scheme is as follows:

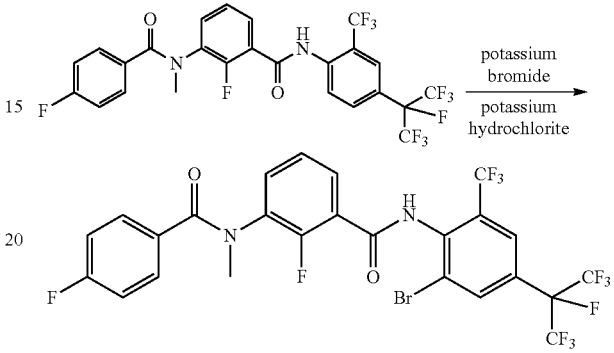

Specifically, it includes the following steps:

To a 1000 mL three-necked flask, 60.2 g (0.1 mol) of N-[2-trifluoromethyl-4-(1,1,1,2,3,3,3-heptafluoroprop-2-yl)-phenyl]-3-[N-methyl-4-fluorobenzamido]-2-fluorobenzamide, 500 g of tert-butanol, 23.8 g (0.2 mol) of potassium bromide, 6.6 g (0.1 mol) of potassium hydroxide, and 50 g of water were added. 181.5 g of 10% potassium hypochlorite solution was added dropwise at 60° C. and the resultant mixture was stirred at 60° C. for 1.5 h. After the reaction was completed, the organic phase was separated, washed with 100 g of 10% sodium sulfite solution, evaporated and dried to obtain 66.8 g of solid brominated product in purity 93.3% and yield 91.5%.

Characterization data: LC/MS [M+1]: m/z=682;
$^1$H-NMR (DMSO-d$_6$, 400 MHz): δ 10.63 (s, 1H), 8.42 (s, 1H), 7.96 (s, 1H), 7.70-7.66 (m, 1H), 7.58 (br s, 1H), 7.39-7.30 (m, 3H), 7.08 (br s, 1H), 3.19 (s, 3H).

Example 9

A bromination method for m-diamide compounds is provided in this example, the scheme is as follows:

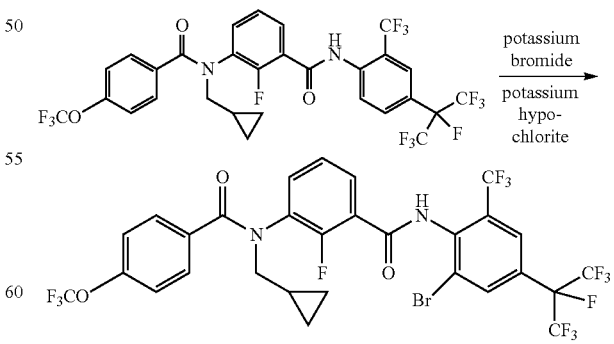

Specifically, it includes the following steps:

To a 1000 mL three-necked flask, 70.8 g (0.1 mol) of N-[2-trifluoromethyl-4-(1,1,1,2,3,3,3-heptafluoroprop-2-yl)-phenyl]-3-[N-(cyclopropylmethyl)-4-trifluoromethoxylbenzamido]-2-fluorobenzamide, 200 g of toluene, 13.1 g (0.11 mol) of potassium bromide, 0.66 g (0.01 mol) of potassium hydroxide, and 40 g of water were added. 147.5 g of 10% potassium hypochlorite solution was added dropwise at 90° C., and the resultant mixture was stirred at 90° C. for 1 h. After the reaction was completed, the organic phase was separated, washed with 100 g of 10% sodium sulfite solution, evaporated and dried to obtain 75.6 g of solid brominated product in purity 92.6% and yield 88.9%.

Characterization data: LC/MS [M+1]: m/z=788;

$^{1}$H-NMR (DMSO-$d_6$, 400 MHz): δ 10.46 (s, 1H), 8.34 (d, J=2.1 Hz, 1H), 7.87 (d, J=2.1 Hz, 1H), 7.65 (t, J=7.4 Hz, 1H), 7.54 (br s, 1H), 7.36 (br s, 2H), 7.29 (br s, 1H), 7.16 (br s, 2H), 3.62 (br s, 2H), 0.95 (br s, 1H), 0.34 (br s, 2H), 0.07 (s, 2H).

Example 10

A bromination method for m-diamide compounds is provided in this example, the scheme is as follows:

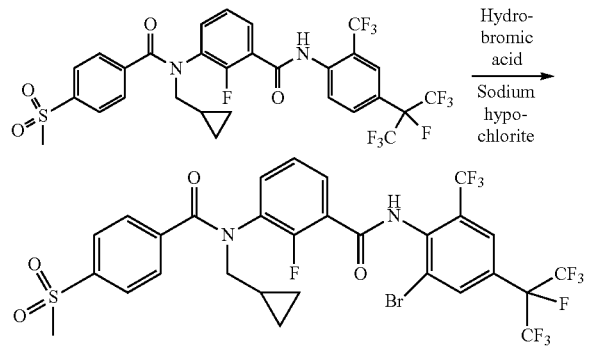

Specifically, it includes the following steps:

To a 1000 mL three-necked flask, 70.3 g (0.1 mol) of 2-fluoro-3-[N-cyclopropylmethyl-4-(methanesulfonyl) benzamido]-N-[2-trifluoromethyl-4-(perfluoropropane-2-yl) phenyl]benzamide, 150 g of 1,2-dichloroethane, 28.4 g (0.14 mol) of 40% hydrobromic acid, 8.4 g (0.2 mol) of sodium hydroxide, and 40 g of water were added. 111.8 g of 10% sodium hypochlorite solution was added dropwise at 70° C. and the resultant mixture was stirred at 70° C. for 1.5 h. After the reaction was completed, the organic phase was separated, washed with 100 g of 10% sodium sulfite solution, evaporated and dried to obtain 75.8 g of solid brominated product in purity 93.0% and yield 90.3%.

Characterization data: LC/MS [M+1]: m/z=783;

$^{1}$H-NMR (DMSO-$d_6$, 400 MHz): δ 10.59 (s, 1H), 8.42 (d, J=2.1 Hz, 1H), 7.95 (d, J=2.1 Hz, 1H), 7.80-7.67 (m, 3H), 7.62-7.52 (m, 3H), 7.35 (s, 1H), 3.75 (s, 2H), 3.16 (s, 3H), 1.03 (s, 1H), 0.53-0.30 (m, 2H), 0.13 (d, J=16.2 Hz, 2H).

Applicant has stated that although the bromination methods for m-diamide compounds have been described by the above examples in the present disclosure, the present disclosure is not limited thereto, that is to say, it is not meant that the present disclosure has to be implemented depending on the above process methods. It will be apparent to those skilled in the art that any improvements made to the present disclosure, equivalent replacements and addition of adjuvant ingredients to the raw materials of the products of the present disclosure, and selections of the specific implementations, etc., all fall within the protection scope and the disclosed scope of the present disclosure.

What is claimed is:

1. A bromination method for m-diamide compounds, wherein the bromination method comprises: reacting a compound represented by formula I with a brominating reagent in the presence of an oxidant to obtain a brominated product represented by formula II, the scheme is as follows:

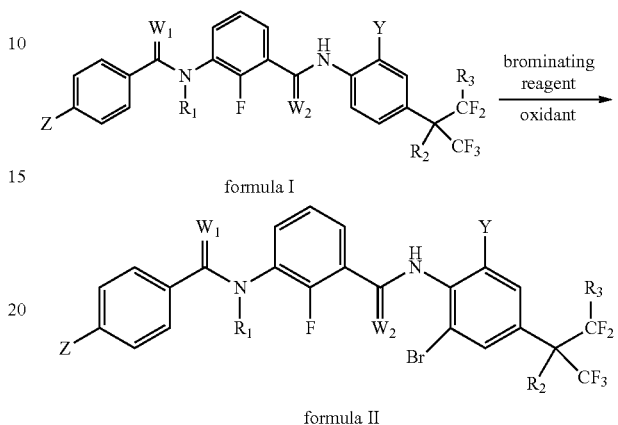

wherein, Z is selected from any one of the group consisting of hydrogen, halogen, cyano, nitro, C1-C6 linear or branched alkyl, halogenated C1-C6 linear or branched alkyl, C1-C6 linear or branched alkoxyl, halogenated C1-C6 linear or branched alkoxyl, C1-C6 alkylsulfonyl, halogenated C1-C6 alkylsulfonyl, C1-C6 alkylsulfinyl, and halogenated C1-C6 alkylsulfinyl;

$W_1$ and $W_2$ are each independently O or S;

$R_1$ is selected from any one of C1-C6 linear or branched alkyl or

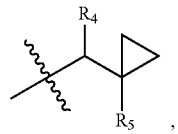

$R_4$ is selected from the group consisting of hydrogen, halogen, C1-C6 linear or branched alkyl, halogenated C1-C6 linear or branched alkyl, C3-C8 cycloalkyl, and halogenated C3-C8 cycloalkyl, $R_5$ is hydrogen or halogen, and the wavy line represents the connecting site of the group;

Y is selected from any one of the group consisting of halogen, C1-C6 linear or branched alkyl, halogenated C1-C6 linear or branched alkyl, C1-C6 linear or branched alkoxyl, and halogenated C1-C6 linear or branched alkoxyl;

$R_2$ is hydrogen, halogen or methoxyl; and $R_3$ is fluoro or trifluoromethyl;

wherein the oxidant is selected from any one or a combination of at least two of the group consisting of a metal perchlorate, metal chlorate, metal hypochlorite, and chlorine; and the molar ratio of the oxidant to the compound represented by formula I is from 0.4:1 to 2.0:1.

2. The bromination method according to claim 1, wherein the brominating reagent is selected from the group consisting of metal bromide, ammonium bromide, bromine, and hydrobromic acid; and the molar ratio of the brominating reagent to the compound represented by formula I is from 0.55:1 to 2.0:1.

3. The bromination method according to claim 2, wherein the metal is an alkali metal or an alkaline earth metal.

4. The bromination method according to claim 3, wherein the brominating reagent is sodium bromide, potassium bromide, bromine or hydrobromic acid.

5. The bromination method according to claim 1, wherein if the oxidant comprises a metal, the metal is an alkali metal or an alkaline earth metal.

6. The bromination method according to claim 5, wherein the oxidant is selected from the group consisting of sodium chlorate, potassium chlorate, sodium hypochlorite, potassium hypochlorite, and chlorine.

7. The bromination method according to claim 1, wherein the reaction is performed in the presence of an alkaline compound; and
the molar ratio of the alkaline compound to the compound represented by formula I is from 0.1:1 to 2.0:1.

8. The bromination method according to claim 7, wherein the alkaline compound is selected from any one or a combination of at least two of the group consisting of metal hydroxide, metal carbonate, metal bicarbonate, and ammonia.

9. The bromination method according to claim 8, wherein if the alkaline compound comprises a metal, the metal is an alkali metal or an alkaline earth metal.

10. The bromination method according to claim 9, wherein the alkaline compound is sodium hydroxide or potassium hydroxide.

11. The bromination method according to claim 1, wherein the reaction is performed in the presence of a solvent and; the solvent is selected from any one or a combination of at least two of the group consisting of haloalkane solvents, aromatic hydrocarbon solvents, alcoholic solvents, chain or cyclic ether solvents, and nitrile solvents and;
wherein, based on 1 mol of the amount of the compound represented by formula I, the amount of the solvent is 500-5000 g.

12. The bromination method according to claim 11, wherein, the haloalkane solvent is selected from any one or a combination of at least two of the group consisting of dichloromethane, 1,2-dichloroethane, chloroform, and carbon tetrachloride;
wherein, the aromatic hydrocarbon solvent is selected from any one or a combination of at least two of the group consisting of benzene, toluene, and xylene;
wherein, the alcoholic solvent is selected from any one or a combination of at least two of the group consisting of methanol, ethanol, n-propanol, isopropanol, n-butanol, isobutanol, and tert-butanol;
wherein, the chain or cyclic ether solvent is selected from any one or a combination of at least two of the group consisting of diethyl ether, tetrahydrofuran, dioxane, and 1,2-dimethoxyethane; and
wherein, the nitrile solvent is selected from any one or a combination of at least two of the group consisting of acetonitrile, propionitrile, and butyronitrile.

13. The bromination method according to claim 1, wherein Z is selected from any one of the group consisting of hydrogen, fluorine, chlorine, bromine, iodine, cyano, nitro, fluorinated C1-C4 linear or branched alkyl, fluorinated C1-C4 linear or branched alkoxyl, C1-C4 alkylsulfonyl, and fluorinated C1-C4 alkylsulfonyl;

wherein, both of $W_1$ and $W_2$ are O;
wherein, $R_1$ is selected from any one of the group consisting of C1-C4 linear or branched alkyl and

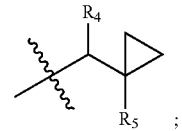

wherein $R_4$ is selected from the group consisting of hydrogen, fluorine, methyl, ethyl, n-propyl, isopropyl, n-butyl, isobutyl, tert-butyl, n-pentyl, 2-pentyl, neopentyl, isopentyl, 4-methyl-2-pentyl, n-hexyl, monofluoromethyl, difluoromethyl, trifluoromethyl, monochloromethyl, dichloromethyl, trichloromethyl, pentafluoroethyl, heptafluoroisopropyl, cyclopropyl, cyclobutyl, cyclopentyl, perfluorocyclopropyl, perfluorocyclobutyl, and perfluorocyclopentyl, and
wherein $R_5$ is hydrogen, fluorine or chlorine, and the wavy line represents the connecting site of the group;
wherein, Y is selected from any one of the group consisting of halogen, C1-C4 linear or branched alkyl, fluorinated C1-C4 linear or branched alkyl, C1-C4 linear or branched alkoxyl, and fluorinated C1-C4 linear or branched alkoxyl;
wherein, $R_2$ is fluorine; and
wherein, $R_3$ is fluorine.

14. The bromination method according to claim 13, wherein, Z is selected from any one of the group consisting of hydrogen, fluorine, chlorine, bromine, iodine, cyano, nitro, trifluoromethyl, pentafluoroethyl, heptafluoroisopropyl, difluoromethoxyl, trifluoromethoxyl, methanesulfonyl, and trifluoromethanesulfonyl;
wherein $R_1$ is methyl, cyclopropylmethyl, wherein $R_4$ and $R_5$ are both hydrogen, or 1-cyclopropylethyl, wherein $R_4$ is methyl and $R_5$ is hydrogen; and
wherein, Y is trifluoromethyl.

15. The bromination method according to claim 1, wherein the temperature of the reaction is 0-150° C. and;
wherein, the reaction time is 0.5-8 hours.

16. The bromination method according to claim 1, wherein the oxidant is added through a pipe or by dropwise addition.

17. The bromination method according to claim 1, wherein the bromination method further comprises the use of a solvent comprising water and post-treatment steps;
wherein, the post-treatment steps include organic phase separation, washing, solvent removal and drying.

18. The bromination method according to claim 17, wherein a sodium sulfite solution is used in the washing step; and
a concentration of the sodium sulfite solution is 5-20% by weight.

19. The bromination method according to claim 1, wherein the bromination method is carried out by: mixing a compound represented by formula I with a solvent comprising water, adding the brominating reagent and an alkaline compound, dropwise adding or charging an oxidant through a pipe at 0-150° C., and then letting the reaction run at 0-150° C. for 0.5-8 hours; and after the reaction is completed, the organic phase is separated, washed with a sodium sulfite solution, evaporated and dried to obtain the brominated product represented by formula II.

* * * * *